United States Patent
Martin et al.

(10) Patent No.: US 11,666,744 B2
(45) Date of Patent: Jun. 6, 2023

(54) MULTI-LUMEN MANIFOLD AND METHOD OF OPERATING A MULTI-LUMEN MANIFOLD

(71) Applicant: BASIS MEDICAL, LLC, Atlanta, GA (US)

(72) Inventors: David A. Martin, Atlanta, GA (US); Timothy P. Sharkey, Marietta, GA (US)

(73) Assignee: BASIS MEDICAL, LLC, Atlanta, GA (US)

( * ) Notice: Subject to any disclaimer, the term of this patent is extended or adjusted under 35 U.S.C. 154(b) by 0 days.

(21) Appl. No.: 15/929,944

(22) Filed: May 29, 2020

(65) Prior Publication Data
US 2021/0370041 A1  Dec. 2, 2021

(51) Int. Cl.
*A61M 39/22* (2006.01)
*A61M 25/10* (2013.01)
*A61B 17/12* (2006.01)
*A61M 25/00* (2006.01)

(52) U.S. Cl.
CPC ..... *A61M 39/223* (2013.01); *A61B 17/12136* (2013.01); *A61B 17/12186* (2013.01); *A61M 25/0097* (2013.01); *A61M 25/1011* (2013.01); *A61B 2217/005* (2013.01); *A61M 2025/105* (2013.01)

(58) Field of Classification Search
CPC ............ A61M 25/1011; A61M 25/105; A61M 39/223; A61M 2025/105; A61B 2217/005; A61B 2217/007; A61B 17/12136; A61B 17/12186
See application file for complete search history.

(56) References Cited

U.S. PATENT DOCUMENTS

| | | | |
|---|---|---|---|
| 4,753,238 A | 6/1988 | Gaiser | |
| 4,844,810 A * | 7/1989 | Richalley | A61M 1/3403 210/321.72 |
| 5,022,399 A | 6/1991 | Biegeleisen | |

(Continued)

FOREIGN PATENT DOCUMENTS

WO    WO 2016/187530 A1    11/2016

OTHER PUBLICATIONS

International Search Report and Written Opinion Application No. PCT/US2016/033510, dated Aug. 5, 2016.

(Continued)

*Primary Examiner* — Laura A Bouchelle
*Assistant Examiner* — John A Doubrava
(74) *Attorney, Agent, or Firm* — Moore & Van Allen PLLC

(57) ABSTRACT

Manifolds and methods of operating manifolds are provided. An example manifold for controlling multi-lumen devices is provided that includes a substance supply mechanism. The substance supply mechanism independently provides a substance to, or remove a substance from, each of a plurality of lumens. The example manifold also includes a lumen selection mechanism. The lumen selection mechanism selectively opens and closes a connection between the substance supply mechanism and at least one of the plurality of lumens. A corresponding method of operation is also provided. An example embodiment also includes a manifold for use with a vessel seclusion device.

17 Claims, 13 Drawing Sheets

(56) References Cited

U.S. PATENT DOCUMENTS

| | | | |
|---|---|---|---|
| 5,224,938 A | 7/1993 | Fenton, Jr. | |
| 5,460,610 A | 10/1995 | Michael | |
| 5,662,609 A | 9/1997 | Slepian | |
| 5,725,535 A | 5/1998 | Hedge et al. | |
| 8,162,879 B2 | 4/2012 | Hattangadi et al. | |
| 8,603,064 B2 | 12/2013 | Hattangadi et al. | |
| 2003/0079752 A1 | 5/2003 | Hart et al. | |
| 2005/0107738 A1* | 5/2005 | Slater | A61M 25/10 604/96.01 |
| 2005/0273050 A1 | 12/2005 | Yokoyama et al. | |
| 2006/0095015 A1 | 5/2006 | Hobbs et al. | |
| 2009/0036830 A1 | 2/2009 | Jablonski et al. | |
| 2009/0203995 A1 | 8/2009 | Matonick | |
| 2009/0318855 A1* | 12/2009 | Ehrenreich | A61M 25/1011 604/35 |
| 2010/0082012 A1 | 4/2010 | Hattangadi et al. | |
| 2010/0298860 A1 | 11/2010 | Thomas | |
| 2011/0218494 A1 | 9/2011 | Gerrans et al. | |
| 2014/0046243 A1 | 2/2014 | Ray et al. | |
| 2014/0150782 A1 | 6/2014 | Vazales et al. | |
| 2014/0163525 A1 | 6/2014 | Stamberg | |
| 2015/0150436 A1* | 6/2015 | Cornhill | A61M 25/1018 600/115 |
| 2015/0174379 A1 | 6/2015 | Bagaoisan et al. | |
| 2015/0190127 A1 | 7/2015 | Madsen et al. | |
| 2015/0209560 A1 | 7/2015 | Teeslink et al. | |
| 2015/0273190 A1 | 10/2015 | Avevor | |
| 2017/0156610 A1 | 6/2017 | Quackenbush et al. | |
| 2017/0172580 A1* | 6/2017 | Martin | A61B 17/12186 |
| 2019/0209176 A1 | 7/2019 | Martin | |
| 2020/0101269 A1 | 4/2020 | Hayes | |
| 2020/0101369 A1 | 4/2020 | Helgesen et al. | |
| 2020/0108234 A1 | 4/2020 | Sanati et al. | |

OTHER PUBLICATIONS

Ninia, Jerry G., "Treatment of Vulvar Varicosities by Injection-Compression Sclerotherapy"; Dermatologic Surgery 1997;23:573-575.

Office Action for Canadian Application No. 2,986,475 dated Sep. 24, 2018, 4 pages.

International Search Report and Written Opinion for PCT/US2021/032193 dated Aug. 31, 2021 (21 pages).

International Preliminary Report on Patentability for corresponding International Application No. PCT/US2021/032193, dated Nov. 17, 2022, 14 pages.

\* cited by examiner

MULTI-LUMEN MANIFOLD AND METHOD OF OPERATING A MULTI-LUMEN MANIFOLD

FIELD OF THE INVENTION

The present disclosure generally relates to multi-lumen medical devices and, more particularly, to methods and apparatuses for controlling multi-lumen medical devices.

BACKGROUND OF THE INVENTION

Current manifolds for multi-lumen assemblies are often large and burdensome to transport and can be difficult to operate. In order for multiple lumens to be activated, conventional manifolds require multiple syringes to provide the multiple lumens with the same substance at the same time. For example, in a catheter application, conventional manifolds do not allow for the balloons to be inflated by the same syringe (e.g., two syringes are needed). Through applied effort, ingenuity, and innovation, many identified problems have been solved by developing solutions that are included in embodiments of the present disclosure, many examples of which are described in detail herein.

SUMMARY OF THE INVENTION

A method, apparatus, and computer program product are provided in accordance with an example embodiment in order to control a multi-lumen device. In an example embodiment, a manifold is provided for controlling a multi-lumen device. The manifold includes a substance supply mechanism. The substance supply mechanism may be configured to independently provide a substance to, or remove a substance from, each of a plurality of lumens. The manifold also includes a lumen selection mechanism. The lumen selection mechanism may be configured to selectively open and close a connection between the substance supply mechanism and at least one of the plurality of lumens.

In some embodiments, the substance supply mechanism includes a balloon inflation mechanism. In such an embodiment, the balloon inflation mechanism may be configured to independently adjust an inflation level of a distal balloon and a proximal balloon of the device via a distal balloon lumen and a proximal balloon lumen respectively. In some embodiments, the lumen selection mechanism includes a balloon selection mechanism. In such an embodiment, the balloon selection mechanism may be configured to selectively open and close a connection between the balloon inflation mechanism and at least one of the distal balloon and the proximal balloon.

In some embodiments, the manifold also includes an aspiration mechanism and an infusion mechanism. In such an embodiment, the aspiration mechanism may be configured to remove at least one of blood, a bodily fluid, a chemical agent for permanently secluding a body vessel, or any combination thereof received from an aspiration port lumen and the infusion mechanism may be configured to provide the chemical agent for permanently secluding a body vessel to an infusion port lumen.

In some embodiments, the balloon selection mechanism includes a balloon selection knob operably coupled to a three-way open/close valve. In such an embodiment, the three-way open/close valve may be operably coupled to the individual distal balloon lumen and the individual proximal balloon lumen. In some embodiments, the balloon selection knob includes a closed first position that closes the connection from the balloon inflation mechanism to both the distal balloon and the proximal balloon; a second position that closes the connection from the balloon inflation mechanism to the distal balloon and opens the connection from the balloon inflation mechanism to the proximal balloon; and a third position that closes the connection from the balloon inflation mechanism to the proximal balloon and opens the connection from the balloon inflation mechanism to the distal balloon.

In some embodiments, the balloon inflation mechanism includes an inflation fluid-filled syringe operably coupled to a balloon inflation port disposed on the manifold. In some embodiments, the balloon inflation mechanism includes a balloon inflation knob operably coupled to an inflation chamber; the inflation chamber houses an inflation fluid; the inflation chamber is disposed inside the manifold; and the inflation chamber includes a plunger that, in operation, is either depressed or retracted in response to adjustment of the balloon inflation knob.

In some embodiments, the manifold may also include an agent dispersal mechanism. In such an embodiment, the agent dispersal mechanism may be configured to cause the infusion mechanism to provide the chemical agent for permanently secluding a body vessel to the infusion port lumen. In some embodiments, the infusion mechanism is disposed inside the manifold.

In another example embodiment, a method is provided for controlling a multi-lumen device. The method includes selectively opening and closing a connection between a substance supply mechanism and at least one of a plurality of lumens to select a lumen via a lumen selection mechanism. The method also includes supplying or removing a substance via the substance supply mechanism to the selected lumen. The substance supply mechanism may be configured to independently provide the substance to, or remove the substance from, each of the plurality of lumens.

In some embodiments, the substance supply mechanism includes a balloon inflation mechanism. In such an embodiment, the balloon inflation mechanism may be configured to independently adjust an inflation level of a distal balloon and a proximal balloon of the device via a distal balloon lumen and a proximal balloon lumen respectively. In some embodiments, the lumen selection mechanism includes a balloon selection mechanism. In such an embodiment, the balloon selection mechanism may be configured to selectively open and close a connection between the balloon inflation mechanism and at least one of the distal balloon and the proximal balloon.

In some embodiments, the method also includes removing, via an aspiration mechanism, at least one of blood, a bodily fluid, a chemical agent, or any combination thereof received from an aspiration port lumen and providing, via an infusion mechanism, the chemical agent to an infusion port lumen. In some embodiments, the balloon selection mechanism includes a balloon selection knob operably coupled to a three-way open/close valve. In such an embodiment, the three-way open/close valve may be operably coupled to the individual distal balloon lumen and the individual proximal balloon lumen.

In some embodiments, the balloon selection knob includes a closed first position that closes the connection from the balloon inflation mechanism to both the distal balloon and the proximal balloon; a second position that closes the connection from the balloon inflation mechanism to the distal balloon and opens the connection from the balloon inflation mechanism to the proximal balloon; and a third position that closes the connection from the balloon inflation mechanism to the proximal balloon and opens the connection from the balloon inflation mechanism to the distal balloon.

In some embodiments, the balloon inflation mechanism includes an inflation fluid-filled syringe operably coupled to a balloon inflation port disposed on the manifold. In some embodiments, the balloon inflation mechanism includes a balloon inflation knob operably coupled to an inflation chamber; the inflation chamber houses an inflation fluid; the inflation chamber is disposed inside the manifold; and the inflation chamber includes a plunger that, in operation, is either depressed or retracted in response to adjustment of the balloon inflation knob.

In some embodiments, the method also includes providing, via the agent dispersal mechanism, the chemical agent to the infusion port lumen. In some embodiments, the infusion mechanism is disposed inside the manifold.

In yet another example embodiment, a body vessel seclusion system is provided. The body vessel seclusion system includes a catheter configured to be moved within a body vessel. The catheter includes a proximal balloon lumen, a distal balloon lumen, an infusion port lumen, and an aspiration port lumen. The system includes a proximal balloon supported by the catheter in communication with the proximal balloon lumen. The system also includes a distal balloon supported by the catheter in communication with the distal balloon lumen. The system further includes at least one infusion port supported by the catheter in communication with the infusion port lumen. The system still further includes at least one aspiration port supported by the catheter in communication with the aspiration port lumen. The system also includes a manifold, such as a manifold discussed herein. The manifold includes a substance supply mechanism. The substance supply mechanism being configured to independently provide a substance to, or remove a substance from, each of the proximal balloon lumen, the distal balloon lumen, the infusion port lumen, and the aspiration port lumen. The manifold also includes a lumen selection mechanism configured to selectively open and close a connection between the substance supply mechanism and at least one of the proximal balloon lumen, the distal balloon lumen, the infusion port lumen, or the aspiration port lumen.

The above summary is provided merely for purposes of summarizing some example embodiments to provide a basic understanding of some aspects of the disclosure. Accordingly, it will be appreciated that the above-described embodiments are merely examples and should not be construed to narrow the scope or spirit of the disclosure in any way. It will be appreciated that the scope of the disclosure encompasses many potential embodiments in addition to those here summarized, some of which will be further described below.

BRIEF DESCRIPTION OF THE DRAWINGS

The description of the illustrative embodiments may be read in conjunction with the accompanying figures. It will be appreciated that, for simplicity and clarity of illustration, elements illustrated in the figures have not necessarily been drawn to scale, unless described otherwise. For example, the dimensions of some of the elements may be exaggerated relative to other elements, unless described otherwise. Embodiments incorporating teachings of the present disclosure are shown and described with respect to the figures presented herein, in which.

DETAILED DESCRIPTION OF THE INVENTION

Figure 1A:
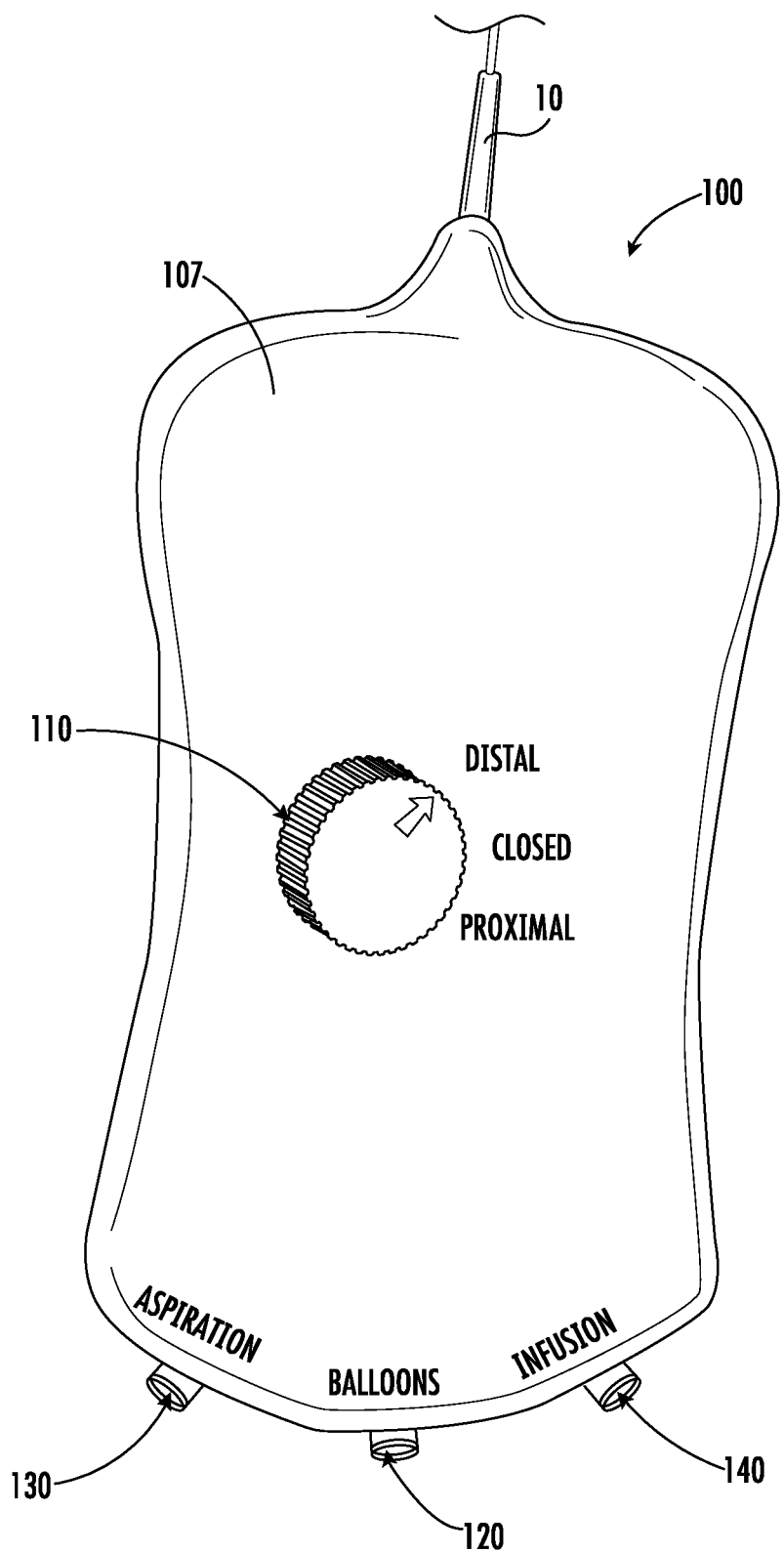
FIGS. 1A-1C illustrate multiple views of both the exterior and interior of a manifold in accordance with an example embodiment of the present disclosure.

Some embodiments of the present disclosure will now be described more fully hereinafter with reference to the accompanying drawings, in which some, but not all embodiments of the disclosure are shown. Indeed, these disclosures may be embodied in many different forms and should not be construed as limited to the embodiments set forth herein; rather, these embodiments are provided so that this disclosure will satisfy applicable legal requirements. Like numbers refer to like elements throughout.

The components illustrated in the figures represent components that may or may not be present in various embodiments of the present disclosure described herein such that embodiments may include fewer or more components than those shown in the figures while not departing from the scope of the present disclosure. Some components may be omitted from one or more figures or shown in dashed line for visibility of the underlying components.

The phrases "in an example embodiment," "some embodiments," "various embodiments," and the like generally mean that the particular feature, structure, or characteristic following the phrase may be included in at least one embodiment of the present disclosure, and may be included in more than one embodiment of the present disclosure (importantly, such phrases do not necessarily refer to the same embodiment).

The word "example" or "exemplary" is used herein to mean "serving as an example, instance, or illustration." Any implementation described herein as "exemplary" is not necessarily to be construed as preferred or advantageous over other implementations.

If the specification states a component or feature "may," "can," "could," "should," "would," "preferably," "possibly," "typically," "optionally," "for example," "often," or "might" (or other such language) be included or have a characteristic, that specific component or feature is not required to be included or to have the characteristic. Such component or feature may be optionally included in some embodiments, or it may be excluded.

In contrast to conventional treatment methods and devices, the exemplary embodiments disclosed herein may be used efficiently, while also being portable. In various embodiments described herein, a manifold is provided in order to control and operate a multi-lumen system. The manifold of example embodiments may be used to selectively interact with a plurality of lumens without the need for multiple infusion mechanisms (e.g., multiple syringes). Various embodiments may be handheld and allow for selective operability of multiple lumens (e.g., distal balloon lumen 124 and proximal balloon lumen 126) with a single infusion mechanism (e.g., syringe). Additionally, various embodiments allow for a compact design that allows the manifold to be easily carried from one place to another. In various embodiments, the manifold described herein may be described for use with a vessel seclusion device However, the manifold of example embodiments may be used for a plurality of lumen-based assemblies, as would be evident to one skilled in the art.

As used herein, the term "body vessel" may comprise any lumen or other similar region in a body, such as a blood vessel or the intestines. Although specific examples are provided herein with reference to veins, one of ordinary skill in the art will recognize that the device and methods disclosed herein are not limited to these particular examples but rather may be employed in any suitable body vessel.

The term "seclusion", as used herein, may refer to the narrowing, collapsing, or closing off of a body vessel. Accordingly, seclusion may be distinct from therapies intended to open or widen a vessel and from therapies intended to prevent the vessel from narrowing.

For ease of reference, exemplary embodiments will be described in terms of use in human subjects. It will be understood, however, that such descriptions are not limited to use in humans but will also include use in other animals unless explicitly stated otherwise. Moreover, although a catheter is referred to herein, one of ordinary skill in the art will recognize that a catheter is merely an exemplary multi-lumen device as disclosed herein.

Figure 1B:
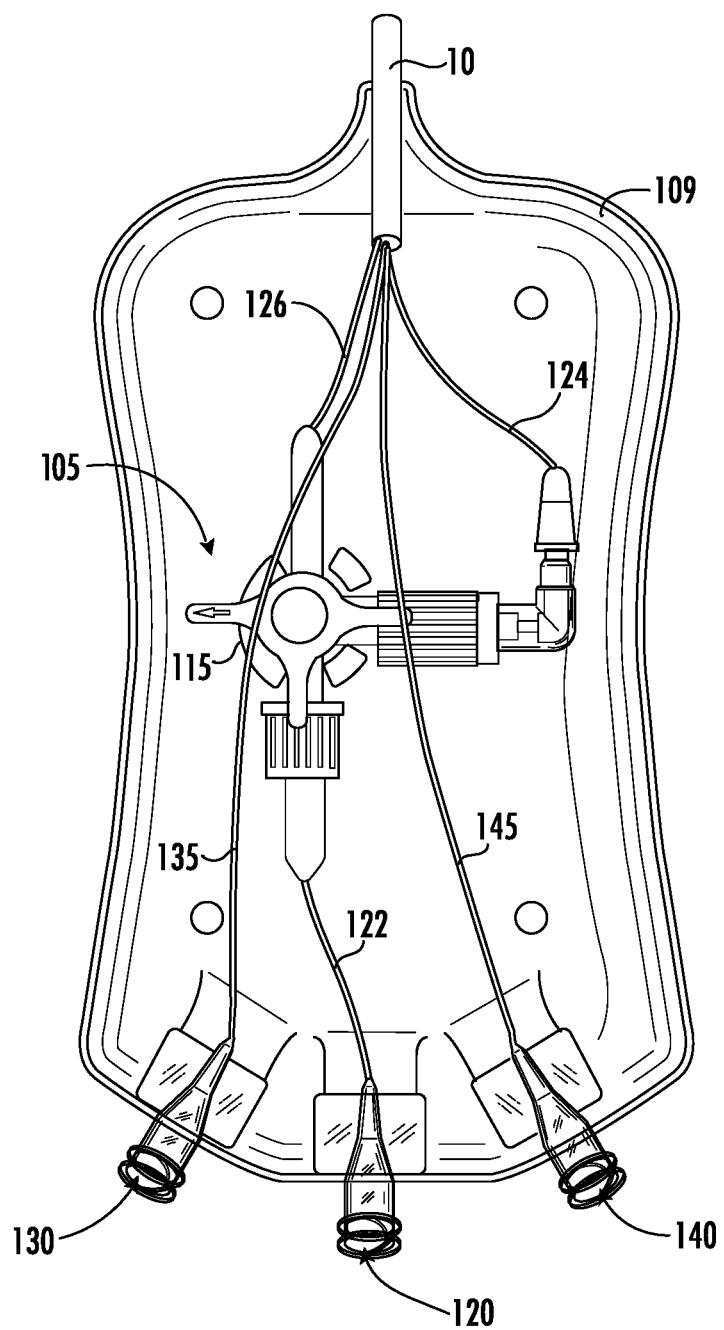
Figure 1C:
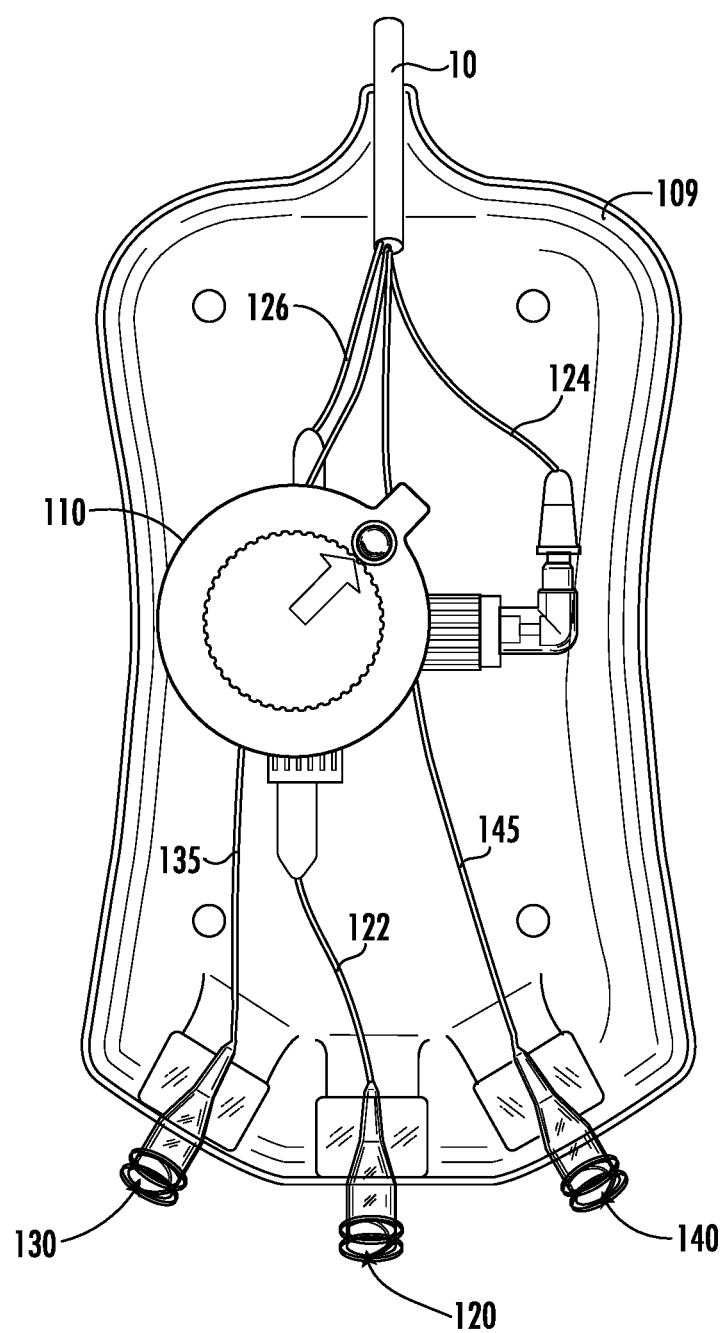

Referring now to FIGS. 1A-1C, a manifold 100 is provided in accordance with an example embodiment of the present disclosure. In various embodiments, the manifold 100 may include a substance supply mechanism (e.g., a syringe 102 for a vessel seclusion device discussed below) and a lumen selection mechanism (e.g., a balloon selection knob 110 and balloon selection valve 115 discussed below in reference to the vessel seclusion device). In various embodiments, the substance supply mechanism may be operably connected to the lumen selection mechanism, such that the lumen selection mechanism may selectively close and open the connection between the substance supply mechanism and each of a plurality of lumens (e.g., balloon lumens 124, 126 in the vessel seclusion device discussed below). Various embodiments of the manifold 100 will be discussed in reference to a vessel seclusion device, but one skilled in the art would understand that the embodiments of the manifold discussed herein may be applied to any multi-lumen assembly.

In various embodiments, the manifold 100 shown in FIGS. 1A-1C may be used with a vessel seclusion device. In some embodiments, the manifold 100 used in a vessel seclusion device may include an aspiration mechanism, an infusion mechanism, a balloon inflation mechanism, and a balloon selection mechanism. In various embodiments, the manifold may have more or less components based on the sophistication of the manifold. For example, a single manifold may be attached to a plurality of lumen assemblies (e.g., multiple lumen assemblies, such as the lumen assembly 10 shown in FIG. 1A). In some embodiments, the manifold 100 may have a casing 105 that includes an upper manifold casing 107 that may be removably attached (e.g., via screws) to a lower manifold casing 109. In some embodiments, the manifold casing 105 (e.g., upper manifold casing 107 and/or lower manifold casing 109), the balloon selection knob 110, and/or the balloon selection valve 115 may be made out of plastic. In various embodiments, the manifold casing 105, the balloon selection knob 110, and/or the balloon selection valve 115 may be made out of a polymer or other material selected to limit reactions with any chemical agents and/or the like.

In some embodiments, the aspiration mechanism may remove at least one of blood, a bodily fluid, a chemical agent (e.g., for permanently secluding a body vessel), or any combination thereof received from an aspiration port lumen 135 of the vessel seclusion device. As shown in FIGS. 1A-1C, the manifold 100 may include an aspiration mechanism connector 130 to allow the aspiration mechanism to be in communication with the aspiration port lumen 135. In various embodiments, the aspiration mechanism may be a syringe 104 that may be removably coupled with (e.g., screwed on) the aspiration mechanism connector 130 to allow the communication between the aspiration mechanism and aspiration port lumen 135 (e.g., to allow the aspiration mechanism to remove at least one of blood, a bodily fluid, a chemical agent for permanently secluding a body vessel, or any combination thereof received from an aspiration port lumen 135 of the vessel seclusion device).

Figure 7A:
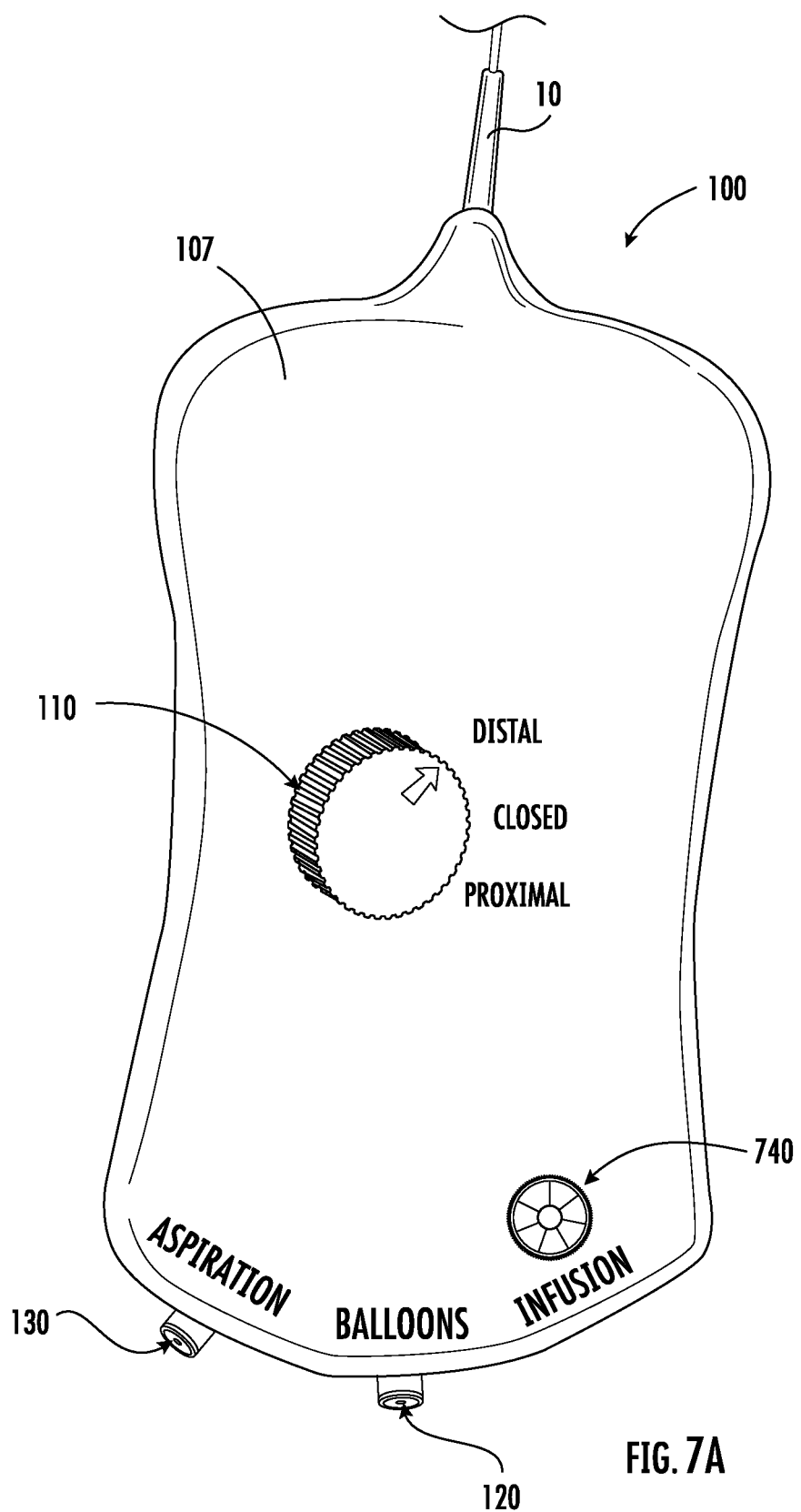
FIGS. 7A-7C illustrate multiple view of both the exterior and interior of a manifold in accordance with an example embodiment of the present disclosure.
Figure 7B:
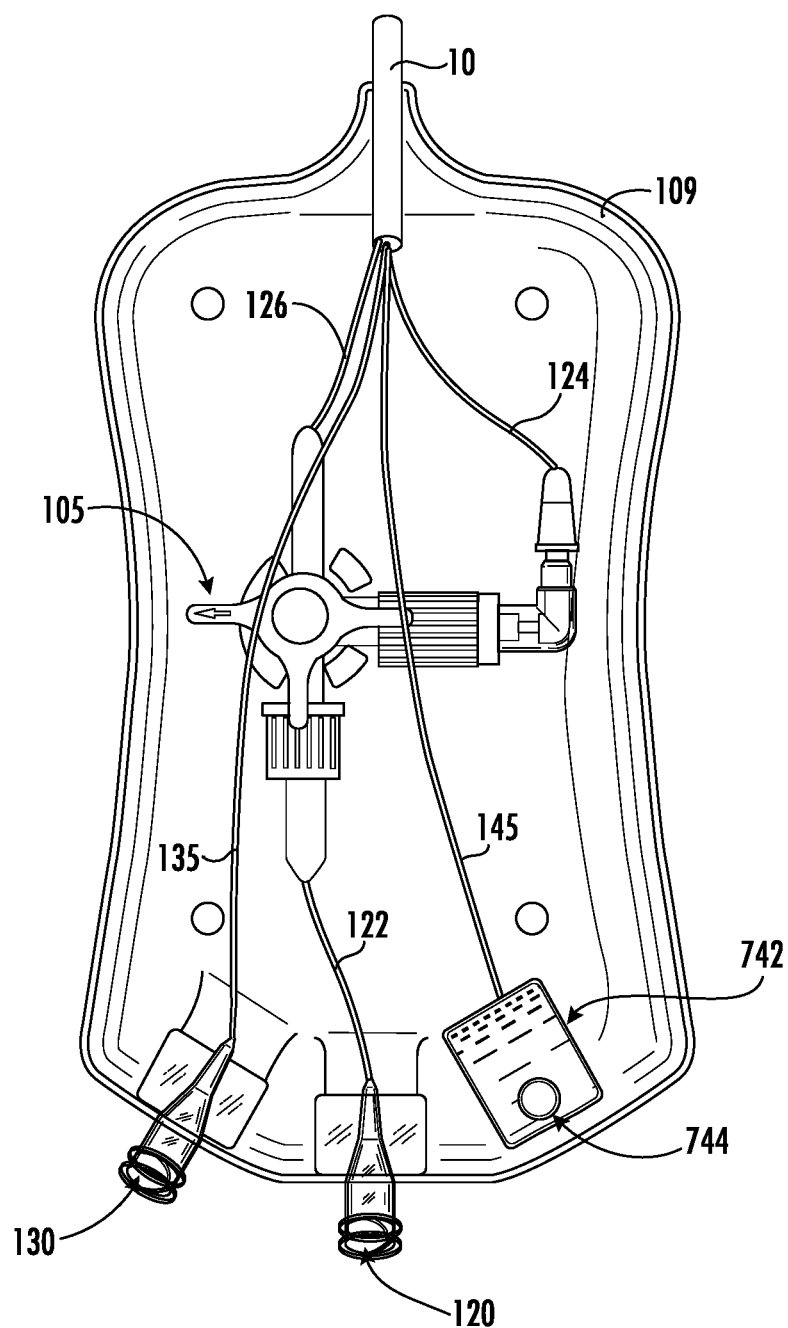
Figure 7C:
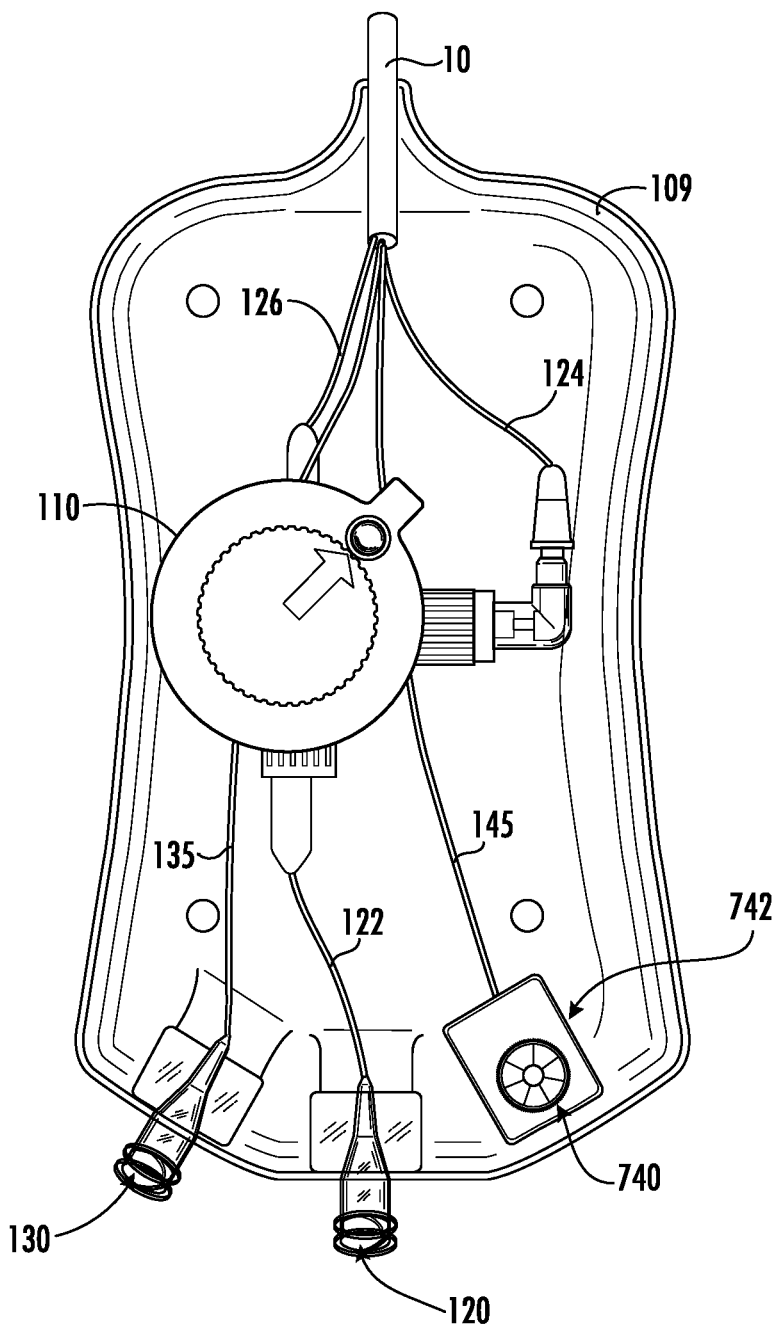

In some embodiments, the infusion mechanism may provide a chemical agent for permanently secluding a body vessel to an infusion port lumen 145 of the vessel seclusion device. In various embodiments, the chemical agent may be a sclerosing agent. In some embodiments, the chemical agent (e.g., sclerosing agent) may be a liquid or a foam. A foam chemical agent may, in some examples, be more visible during operation within the body vessel than other types of chemical agents. As shown in FIGS. 1A and 1B, the manifold 100 may include an infusion mechanism connector 140 to allow the infusion mechanism to be in communication with the infusion port lumen 145. In various embodiments, the infusion mechanism may be a syringe 106 that may removably couple with the infusion mechanism connector 140 to allow the communication between the infusion mechanism and infusion port lumen 145 (e.g., to allow the infusion mechanism to provide a chemical agent for permanently secluding a body vessel to an infusion port lumen 145 of the vessel seclusion device). In some embodiments, for example, as shown in FIGS. 7A-7C, the infusion mechanism may be located within the manifold 100. For example, the infusion mechanism may define an infusion tank 742 located within the manifold containing the chemical agent for permanently secluding a body vessel. In such embodiments, the infusion port lumen 145 may be in communication with the infusion tank 742. In some embodiments, the manifold 100 includes an agent dispersal mechanism. In some embodiments, the agent dispersal mechanism may be provided to cause the infusion mechanism to provide the chemical agent for permanently secluding a body vessel to the infusion port lumen 145. For example, in embodiments in which the infusion mechanism may be disposed within the casing, the agent dispersal mechanism may be disposed at least partially on the exterior of the manifold casing, such that a user may activate the infusion mechanism. Alternatively, the agent dispersal mechanism may be the plunger 108 on a syringe 106, as shown in FIG. 1A. In some embodiments, the agent dispersal mechanism may include a screw-down valve 740 configured to engage a plunger 744 within the infusion tank 742.

In some embodiments, the balloon inflation mechanism may independently adjust an inflation level of a distal balloon 30 and/or a proximal balloon 20 of the vessel seclusion device via a distal balloon lumen 124 and/or a proximal balloon lumen 126 respectively. In some embodiments, the manifold 100 may include a balloon inflation port 120 to allow communication between the balloon inflation mechanism and the balloon selection mechanism. In some embodiments, the balloon inflation mechanism may be a syringe 102 that may be removably coupled with the balloon inflation port 120 to allow the communication between the balloon inflation mechanism and the balloon selection mechanism. In some embodiments, the syringe may be fluid-filled (e.g., filled with a saline solution, radio-opaque dye, and/or the like). In some embodiments, as shown in FIGS. 1B and 1C, the balloon inflation port 120 may be attached to a balloon inflation mechanism lumen 122. In some embodiments, the balloon inflation mechanism lumen 122 may allow communication between the balloon inflation mechanism and the distal balloon lumen 124 and/or the proximal balloon lumen 126 by way of the balloon selection mechanism discussed below (e.g., to allow the inflation mechanism to independently adjust an inflation level of a distal balloon and/or a proximal balloon of the vessel seclusion device via a distal balloon lumen 124 and/or a proximal balloon lumen 126 respectively).

Figure 6A:
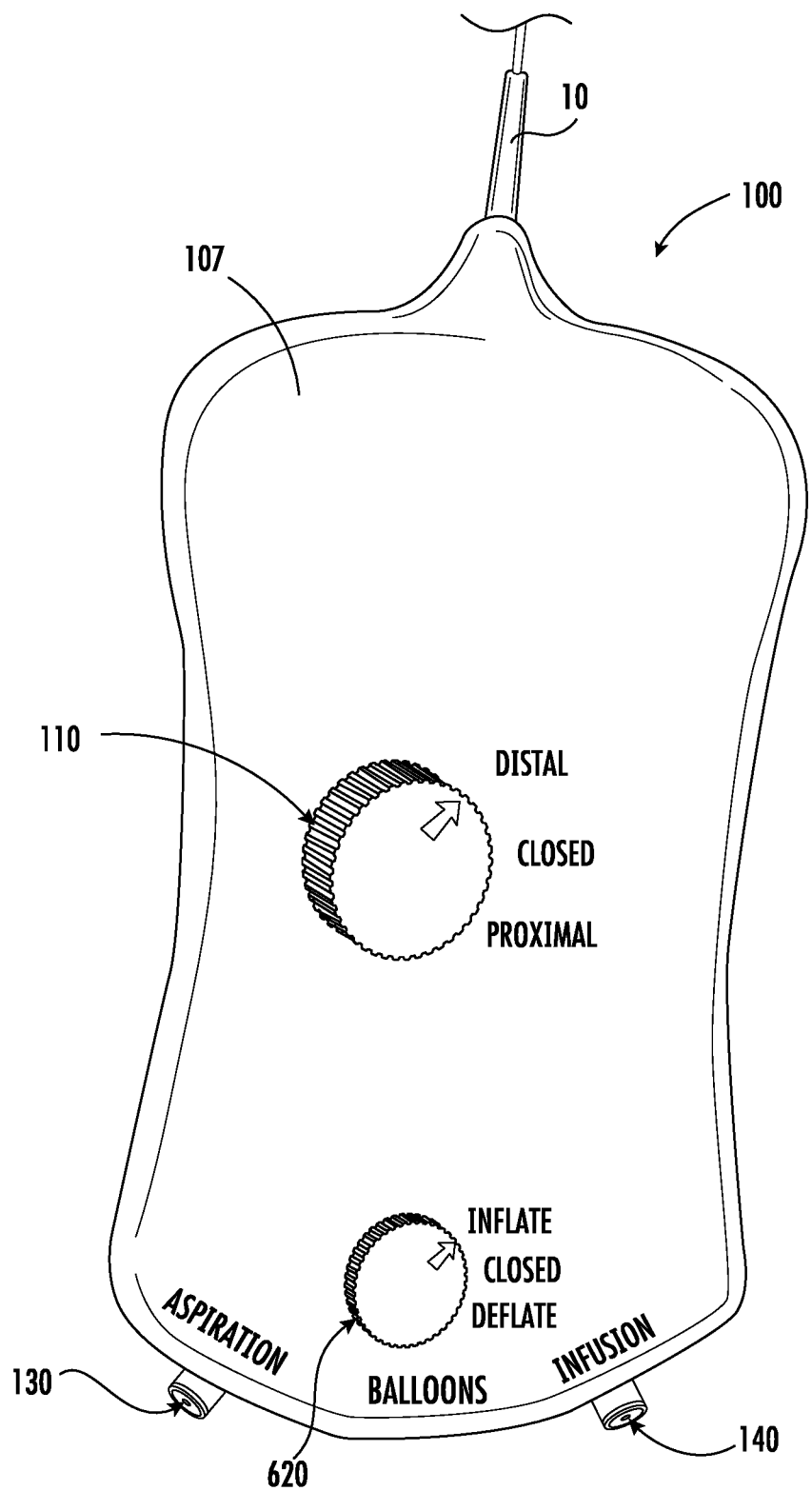
FIGS. 6A-6C illustrate multiple view of both the exterior and interior of a manifold in accordance with an example embodiment of the present disclosure.
Figure 6B:
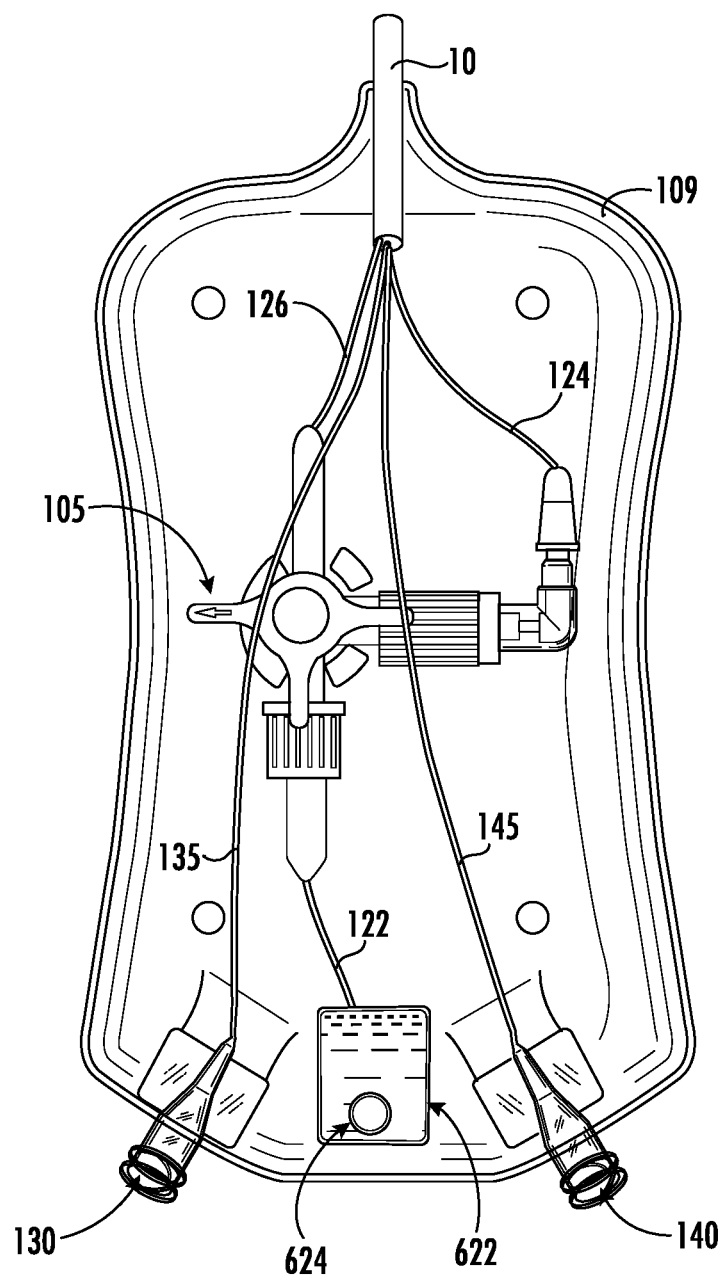
Figure 6C:
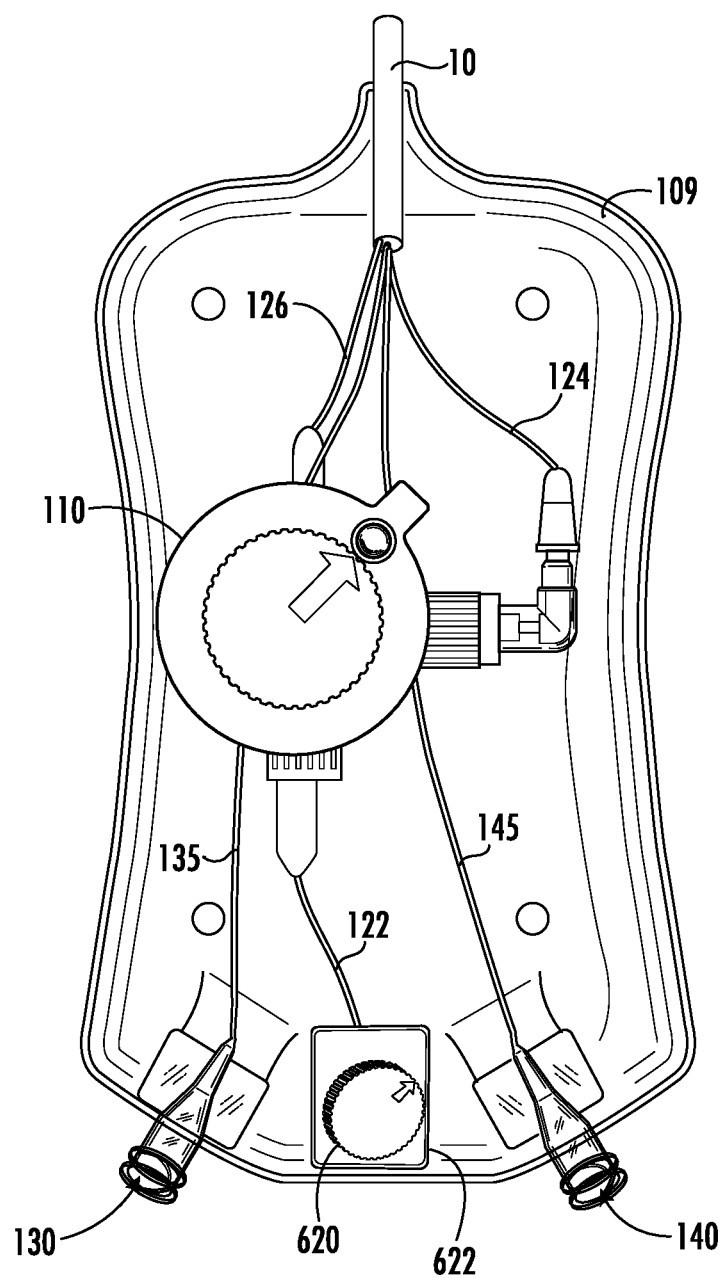

In some embodiments, for example, as shown in FIGS. 6A-6C, the balloon inflation mechanism may include a balloon inflation knob 620 operably coupled to an inflation chamber 622. In some embodiments, the inflation chamber 622 may be disposed inside of the manifold. In some embodiments, the inflation chamber 622 may house an inflation fluid (e.g., saline solution or air). For example, one or both of the balloons may be inflated with air. In some embodiments in which one or both balloons are inflated with air, the air may, in some examples, be visible via an ultrasound better than other potential inflation fluids. In some embodiments, the inflation chamber 622 may include a plunger 624 that, in operation, may be either depressed or retracted in response to adjustment of the balloon inflation knob 620. In such an embodiment, the inflation chamber 622 may be coupled to the balloon inflation mechanism lumen 122 (e.g., at the end of the balloon inflation mechanism lumen 122 that is attached to the balloon inflation port 120 in the non-inflation chamber embodiments shown in FIGS. 1B and 1C.

Figure 5A:
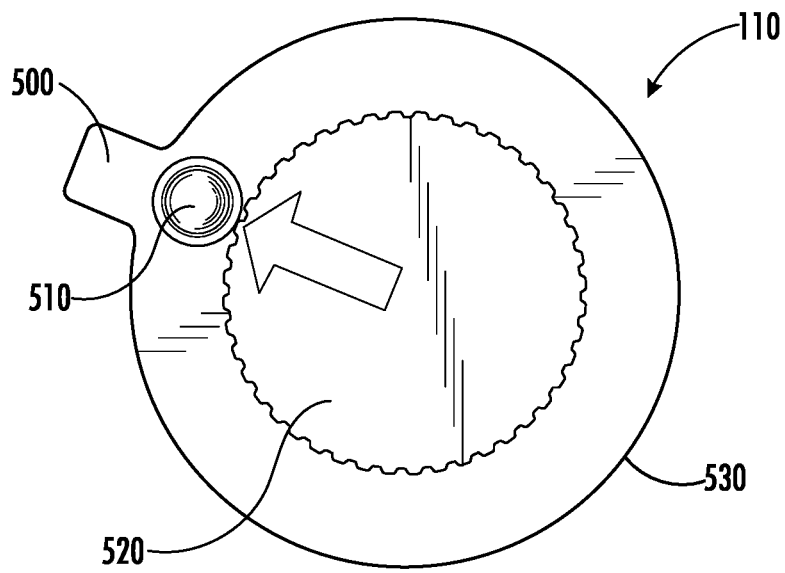
FIGS. 5A-5B illustrate multiple views of a balloon selection knob, such as the one shown in FIGS. 1A-1C, in accordance with an example embodiment of the present disclosure.
Figure 5B:
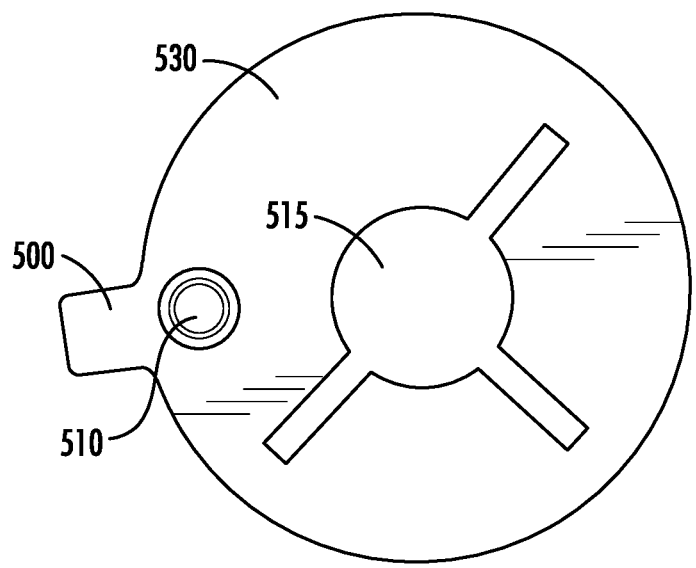

In some embodiments, the balloon selection mechanism may allow for selective opening and closing of a connection between the balloon inflation mechanism and at least one of the distal balloon and the proximal balloon. In some embodiments, the balloon selection mechanism includes a balloon selection knob 110 (shown in FIG. 1A) protruding through the upper manifold casing 107 (e.g., to allow a user to rotate the balloon selection knob via the engagement portion 520 of the balloon selection knob 110). In various embodiments, the balloon selection mechanism may be any type of selection mechanism, such as a sliding switch, a dial, or the like. In some embodiments, the balloon selection knob 110 may be operably coupled to the balloon selection valve 115 (e.g., three-way open/close valve) (shown without the upper manifold casing in FIG. 1C). In an example embodiment, as shown in FIG. 5A, the balloon selection knob 110 may include an engagement portion 520 and an interior portion 530. As shown in FIG. 5B, the interior portion 520 of the balloon selection knob 110 may include a recess 510 configured to couple with the balloon selection valve 115. In an example embodiment, the balloon selection knob 110 may be coupled to the balloon selection valve 115 (as shown in FIG. 1C). In some embodiments, the upper manifold casing 107 may define a hole to receive the engagement portion 520 of the balloon selection knob 110. In some embodiments, the diameter of the interior portion 530 of the balloon selection knob 110 may be larger than the diameter of the hole defined in the upper manifold casing 107, such that when the upper manifold casing 107 is attached to the lower manifold casing 109, the balloon selection knob 110 motion is restricted in the vertical direction.

In some embodiments, the balloon selection knob 110 may be coupled to the balloon selection valve 115 (e.g., such as by the recess 515), such that the rotation of the engagement portion 520 of the balloon selection knob 110 also may rotate the balloon selection valve 115 between the positions discussed below. In some embodiments, the balloon selection knob 110 may include a restricting protrusion 500 and/or ball detent plunger 510 to restrict the rotation motion of the balloon selection knob 110. In an example embodiment, the restricting protrusion 500 may be a part of the interior portion 530 of the balloon selection knob 110. In some embodiments, the upper manifold casing 107 may include one or more stopping pegs to engage the restricting protrusion 500 of the balloon selection knob. For example, the valve 115 may be capable of 360 degrees of rotation, but the desired use (e.g., independently adjusting the distal balloon and proximal balloon may use less than the full 360 degrees of rotation (e.g., 120 degrees of rotation). In some embodiments, the ball detent plunger 510 may be positioned on the interior portion 530 of the balloon selection knob 110. In some embodiments, the ball detent plunger 510 may be used to temporarily restrict the rotational movement of the balloon selection knob 110. In some embodiment, the ball detent plunger 510 may include a sphere (e.g., a metal sphere) that may slide within a bored cylinder against the pressure of a spring. In such an embodiment, the pressure of the spring pushes the ball against a detent or catch to temporarily restrict the movement of an object (e.g., the balloon selection knob 110). In some embodiments, the interior of the upper manifold casing 107 may include one or more detents or catches to engage the ball detent plunger 510. In an example embodiment, the number of detents may be based on the number of valve positions used. For example, the vessel seclusion device discussed below may have 3 positions and the upper manifold casing 107 may have a detent for each position. In an example embodiment, the pressure of the spring may be strong enough to hold the balloon selection knob 110 in place until the balloon selection knob is rotated by a user.

In some embodiments, the balloon selection valve 115 may be a three-way open/close valve. In some embodiments the balloon selection valve 115 may be a T-shaped three-way open/close valve. In some embodiments, the balloon selection valve 115 may be a faucet valve or the like. In some embodiments, the balloon selection valve 115 may be in communication with the balloon inflation mechanism lumen 122, the distal balloon lumen 124, and the proximal balloon lumen 126. In some embodiments, the balloon selection knob 110, and subsequently the valve 115, may have a closed first position 150, a second position 155, and a third position 160. In some embodiments, the closed first position 150 may be such that the valve 115 closes, or leaves closed, (e.g., blocks) the connection between the balloon inflation mechanism lumen 122 and both the distal balloon lumen 124 and the proximal balloon lumen 126. In some embodiments, the second position 155 may be such that the valve 115 closes, or leaves closed, (e.g., blocks) the connection between the balloon inflation mechanism lumen 122 and the distal balloon lumen 124, while opening, or leaving open, the connection between the balloon inflation mechanism lumen 122 and the proximal balloon lumen 126. In some embodiments, the third position 160 may be such that the valve 115 closes, or leaves closed, (e.g., blocks) the connection between the balloon inflation mechanism lumen 122 and the proximal balloon lumen 126, while opening, or leaving open, the connection between the balloon inflation mechanism lumen 122 and the distal balloon lumen 124. In some embodiments, the upper manifold casing 107 may define a detent to engage with the ball detent plunger 510 at each of the three positions described above.

Figure 2:
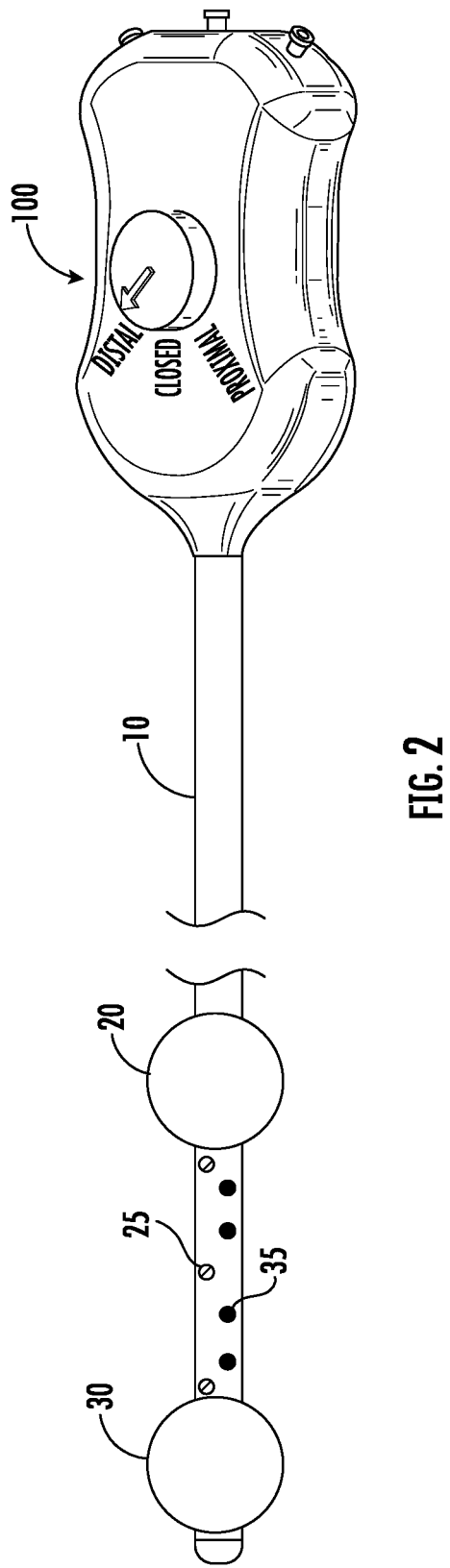
FIG. 2 illustrates a device for secluding a body vessel ("vessel seclusion device") including a manifold, such as the manifold shown in FIGS. 1A-1C, in accordance with an example embodiment of the present disclosure.

Referring now to FIG. 2, a schematic drawing of the vessel seclusion device according to an example embodiment is provided. In various embodiments, the manifold 100 is provided in accordance with an example embodiment as a part of the vessel seclusion device shown. As shown in FIG. 2, for example, the device may be a catheter attached to the manifold 100 discussed in FIGS. 1A-1C. The catheter may include a lumen assembly 10, a proximal balloon 20, at least one infusion port 25, a distal balloon 30, and at least one aspiration port 35. During operation within a body vessel, the proximal balloon 20 and the distal balloon 30 may define a treatment chamber therebetween inside of the body vessel when the balloons 20, 30 are inflated. In this regard, for example, a chemical agent may be introduced into the treatment chamber to seclude the body vessel within the treatment chamber. The balloons 20, 30 may be made of any suitable material as understood by one of ordinary skill in the art including, but not limited to, polymeric materials. In some embodiments, the balloons 20, 30 may be configured to be strong enough to resist the contraction of the body vessel during operation. In accordance with certain embodiments, for example, the body vessel may include at least one of a varicose vein, a portal vein, a perforator vein, a superficial vein, a peripheral vein, an arteriovenous malformation, or any combination thereof. The catheter may be of any length suitable for secluding a variety of body vessels as understood by one of ordinary skill in the art (e.g., 100 cm).

The lumen assembly 10 may include the distal balloon lumen 124, the proximal balloon 126, the aspiration port lumen 135, and the infusion port lumen 145. In some embodiments, the lumen assembly 10 may include a guide wire, although a guide wire is not required. In various embodiments, the individual lumens (e.g., lumens 124, 126, 135, 145) may not be very flexible. For example, the individual lumens within the lumen assembly 10 may only bend and/or move from about 2 mm to about 3 mm. However, the lumen assembly 10 may be sufficiently flexible to navigate through the body vessels of an individual. For instance, the lumen assembly 10 may be used to guide the device into position inside the body vessel.

In accordance with certain embodiments, for instance, the lumen assembly 10 may include the infusion port 25 and the aspiration port 35 to introduce and evacuate fluids respectively. In certain embodiments, for example, the infusion port 25 and the aspiration port 35 may be positioned on the lumen assembly 10 within the treatment chamber created by the inflated proximal balloon 20 and the distal balloon 30. In some embodiments, for example, each aspiration port 35 and/or infusion port 25 may include a port orifice and a one-way valve at the port orifice. In this regard, for instance, the aspiration port 35 may evacuate blood and other bodily fluids from the treatment chamber to provide an empty area for the chemical agent to occupy and to prevent the chemical agent from being diluted. In some embodiments, the aspiration port 35 may remove the blood and other bodily fluids from the treatment chamber via the aspiration mechanism discussed above in reference to FIGS. 1A-1C. Additionally, each aspiration port 35 may evacuate the chemical agent from the treatment chamber after treatment. Moreover, the infusion port 25 may introduce the chemical agent into the treatment chamber to initiate seclusion of the body vessel. In some embodiments, the infusion port 25 may introduce the chemical agent provided by the infusion mechanism discussed above in reference to FIGS. 1A-1C. Various embodiments of the present disclosure may be used with the operations discussed in U.S. patent application Ser. No. 14/978,021 filed on Dec. 22, 2015, U.S. patent application Ser. No. 16/276,884 filed on Feb. 15, 2019, U.S. patent application Ser. No. 15/929,937 filed on May 29, 2020, and PCT Application Number PCT/US2016/033510 filed on May 20, 2016, which are all incorporated herein by reference.

In various embodiments, a visualization device (e.g., an ultrasound transducer) may be used during the operation of the catheter. For example, the ultrasound transducer may be used to position the catheter within a body vessel. In various embodiments, one or more substances used in the catheter may be visible via ultrasound, such that the movement and operation of the body vessel seclusion system may be monitored during operation. For example, the ultrasound transducer may be used to monitor the contraction and/or deflection of the body vessel in an instance the balloons are inflated and the treatment chamber is defined (e.g., a vein may deflect approximately 1 mm in an instance in which the vein is prepared for seclusion).

In various embodiments, the visualization device (e.g., the ultrasound transducer) may be used to monitor the operation of the body vessel seclusion system in approximately real-time. In various embodiments, the visualization device (e.g., the ultrasound transducer) may monitor the balloon inflation during operation (e.g., the balloons may be filled with a substance visible under an ultrasound, such as air). In various embodiments, the visualization device (e.g., the ultrasound transducer) may be used to position the catheter within the body vessel (e.g., originally for the first treatment chamber and/or during repositioning for subsequent treatment chambers). For example, the catheter may include a reflective substance such that at least a portion of the catheter may be visible via an ultrasound. In various embodiments, the visualization device may be used to monitor the infusion and/or aspiration of the chemical agent into the body vessel during operation. For example, the chemical agent may be visible by the visualization device, such that the amount of chemical agent in the body vessel and area of coverage can be monitored (e.g., a doctor may, in some examples, be able to determine when a sufficient amount of chemical agent has been provided to the body vessel for seclusion).

Figure 3:
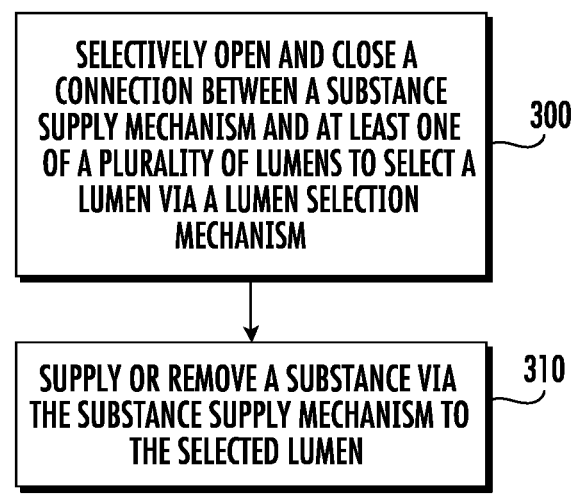
FIG. 3 is a flowchart illustrating the method of operation for an example manifold in accordance with an example embodiment of the present disclosure.

Referring now to FIG. 3, a flowchart illustrating a method of operating a manifold in accordance with an example embodiment of the present disclosure is provided. The operations in FIG. 3 are more fully described in reference to example embodiments of the manifold for the vessel seclusion device discussed in FIG. 4.

Referring now to Block 300 of FIG. 3, the method includes selectively opening and closing a connection between a substance supply mechanism and at least one of a plurality of lumens to select a lumen via a lumen selection mechanism. As discussed above in reference to FIGS. 1A and 1B, the lumen selection mechanism may selectively open and close a connection between the substance supply mechanism and at least one of the plurality of lumens. Blocks 400 and 440 of FIG. 4, discussed in more detail below, may be an applied version of this step for a method of controlling a vessel seclusion device. For example, the balloon selection mechanism discussed below may allow for a user to select at least one of a plurality of lumens (distal balloon lumen 124 and/or proximal balloon lumen 126) to supply a substance (e.g., a fluid such as saline).

As discussed above, the manifold 100 may include a substance supply mechanism (e.g., a syringe for a vessel seclusion device) and a lumen selection mechanism (e.g., a balloon selection knob 110 and balloon selection valve 115). In various embodiments, the substance supply mechanism may be operably connected to the lumen selection mechanism, such that the lumen selection mechanism may selectively close and open the connection between the substance supply mechanism and each of a plurality of lumens (e.g., balloon lumens 124, 126 in the vessel seclusion device). For example, the lumen selection mechanism may be a valve configured to selectively connect the substance supply mechanism with one or more lumens of the plurality of lumens. In some embodiments, the substance supply mechanism may be configured to independently provide a substance to, or remove a substance from, each of a plurality of lumens.

Referring now to Block 310 of FIG. 3, the method includes supplying or removing a substance via the substance supply mechanism to the selected lumen. As discussed above, in some embodiments the substance supply mechanism may be operably coupled each of the plurality of lumens to remove and/or supply the substance to the lumen selected using the lumen selection mechanism. For example, the substance supply mechanism may be a syringe operably coupled to the manifold 100 such that the substance may be supplied and/or removed from the selected lumen based on the position of the syringe plunger.

Figure 4:
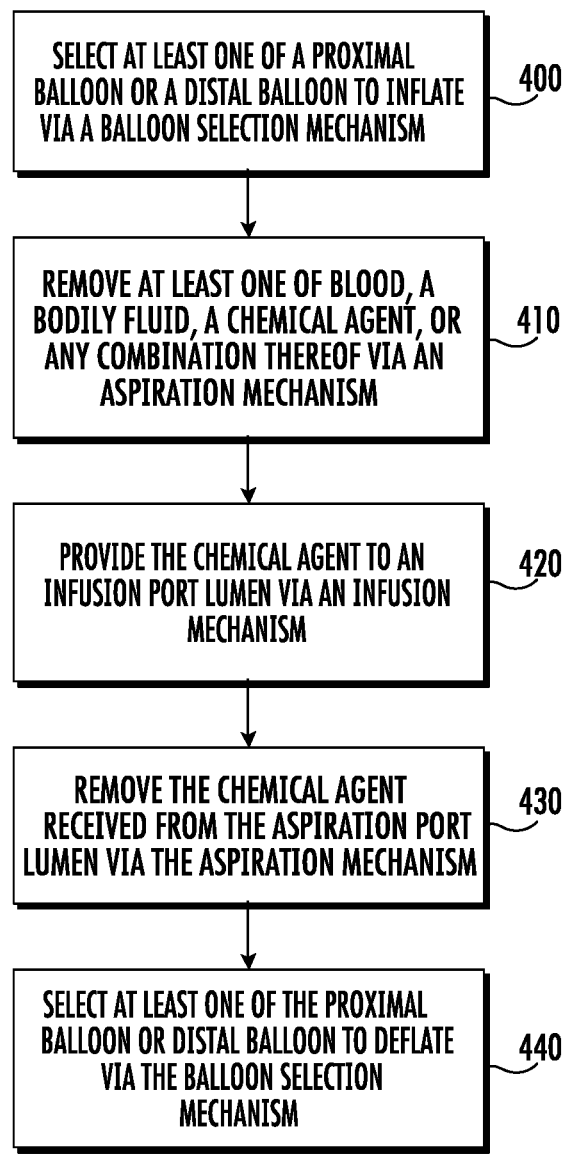
FIG. 4 is a flowchart illustrating the method of operation for a vessel seclusion device with a manifold, such as the one shown in FIGS. 1A-2, in accordance with an example embodiment of the present disclosure.

Referring now to FIG. 4, a flowchart illustrating a method of operating a seclusion device via a manifold in accordance with an example embodiment of the present disclosure is provided. Unless otherwise noted, the operations described may be accomplished using various embodiments described herein. FIGS. 1A, 1B, 1C, and 2 are referenced during the description of FIG. 4 and illustrate the manifold of an example embodiment. As discussed above, the method of operating the seclusion device via a manifold may be used for the seclusion device and methods discussed in U.S. patent application Ser. No. 14/978,021 filed on Dec. 22, 2015, U.S. patent application Ser. No. 16/276,884 filed on Feb. 15, 2019, and PCT Application Number PCT/US2016/033510 filed on May 20, 2016, which are incorporated by reference.

Referring now to Block 400 of FIG. 4, the method includes selecting at least one of a proximal balloon 20 or a distal balloon 30 to inflate via a balloon selection mechanism. In some embodiments, the balloon selection mechanism may selectively allow or block a connection between the balloon inflation mechanism and at least one of the distal balloon 30 or the proximal balloon 20. In some embodiments, the balloon selection mechanism may include the balloon selection knob 110 operably coupled to a balloon selection valve 115 (e.g., a three-way open/close valve). In various embodiments, balloon selection valve 115 (e.g., the three-way open/close valve) may be operably coupled to the individual distal balloon lumen 124 and the individual proximal balloon lumen 126. In various embodiments, the balloons 20, 30 may be independently adjusted (e.g., inflated and/or deflated) via the balloon inflation mechanism. In some embodiments, the balloon inflation mechanism (e.g., a syringe) may be removably coupled with the balloon inflation port 120 to communicate with the balloon selection mechanism (e.g., balloon selection valve 115) and subsequently the distal balloon lumen 124 and/or the proximal balloon lumen 126.

In various embodiments, the balloon inflation mechanism may include an inflation chamber. In some embodiments, the inflation chamber may house an inflation fluid (e.g., saline or air). In some embodiments, the inflation chamber may be disposed inside the manifold. In some embodiments, the balloon inflation mechanism may include a balloon inflation knob operably coupled to the inflation chamber, such as via a valve. In some embodiments, the inflation chamber may include a plunger that, in operation, may be either depressed or retracted in response to adjustment of the balloon inflation knob.

As discussed in more detail above in reference to FIG. 1A-1C, the balloon selection mechanism (e.g., the balloon selection knob 110 and, subsequently, the balloon selection valve 115) may define three positions. In some embodiments, the closed first position 150 may be an instance in which the connection from the balloon inflation mechanism to both the distal balloon 30 and the proximal balloon 20 is closed. In some embodiments, the second position 155 may be an instance in which the connection from the balloon inflation mechanism to the distal balloon 30 is closed and the connection from the balloon inflation mechanism to the proximal balloon 20 is opened. In some embodiments, the third position 160 may be an instance in which the connection from the balloon inflation mechanism to the proximal balloon 20 is closed and the connection from the balloon inflation mechanism to the distal balloon 30 is opened.

Referring now to Block 410 of FIG. 4, the method includes removing at least one of blood, a bodily fluid, or any combination thereof via the aspiration mechanism. As discussed in more detail in reference to FIGS. 1A-1C, the aspiration mechanism may remove at least one of blood, a bodily fluid, a chemical agent, or any combination thereof for permanently secluding a body vessel received from an aspiration port lumen of the vessel seclusion device. In some embodiments, the aspiration mechanism may be removably coupled to the aspiration mechanism connector 130 allowing the aspiration mechanism (e.g., a syringe) to be in communication with the aspiration port lumen 135.

Referring now to Block 420 of FIG. 4, the method includes providing the chemical agent to an infusion port lumen via the infusion mechanism. In some embodiments, the chemical agent may be used to permanently seclude a portion of a body vessel. As discussed in more detail above in reference to FIGS. 1A-1C, the infusion mechanism may provide the chemical agent for permanently secluding a body vessel to an infusion port lumen of the vessel seclusion device. In some embodiments, the infusion mechanism may be removably coupled to the infusion mechanism connector 140 allowing the infusion mechanism (e.g., a syringe) to be in communication with the infusion port lumen 145. In some embodiments, the infusion mechanism may be inside of the manifold casing, such that the infusion tank may be defined containing the chemical agent. In some embodiments, the method may also include providing, via the agent dispersal mechanism, the chemical agent for permanently secluding a body vessel to the infusion port lumen 145. In some embodiments, the agent dispersal mechanism may be configured to activate the infusion mechanism in an instance the infusion mechanism is housed within the manifold casing. For example, the agent dispersal may be a button and/or knob on the exterior of the manifold in communication with the infusion mechanism.

Referring now to Block 430 of FIG. 4, the method includes removing the chemical agent received from the aspiration port lumen via the aspiration mechanism. In some embodiments, the chemical agent may be removed via the aspiration port lumen, and subsequently the aspiration mechanism. In various embodiments, the removal of the chemical agent may operate in the same manner as the removal of blood or a bodily fluid via the aspiration mechanism discussed in reference to Block 410 of FIG. 4 above.

Referring now to Block 440 of FIG. 4, the method includes selecting at least one of the proximal balloon or distal balloon to deflate via the balloon selection mechanism. In various embodiments, the selection of the balloons to deflate is the same as the selection of the balloons to inflate discussed in reference to Block 400 of FIG. 4 above. In various embodiments, the balloon inflation mechanism may be capable of both inflating and deflating the balloons (e.g., to either provide a fluid, such as saline, to the balloon(s) or remove the fluid from the balloon(s)).

Various embodiments of the present disclosure allow a user to control a multi-lumen assembly (e.g., a vessel seclusion device) via a handheld manifold. The exemplary embodiments disclosed herein may be used efficiently, while also being portable. In various embodiments described herein, a manifold is provided in order to control and operate a multi-lumen system. The manifold of example embodiments may be used to selectively interact with a plurality of lumens without the need for multiple infusion mechanisms (e.g., multiple syringes). Various embodiments may be handheld and allow for selective operability of multiple lumens (e.g., distal balloon lumen 124 and proximal balloon lumen 126) with a single infusion mechanism (e.g., syringe). Additionally, various embodiments allow for a compact design that allows the manifold to be easily carried from one place to another. In various embodiments, the manifold described herein may be described for use with secluding a body vessel. However, the manifold of example embodiments may be used for a plurality of multi-lumen-based assemblies, as would be evident to one skilled in the art.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

What is claimed is:

1. A method of controlling a multi-lumen device, the method comprising:
   selectively coupling a substance supply mechanism to a manifold having a manifold casing, the manifold casing comprising an aspiration mechanism connector, an infusion mechanism connector, and a balloon inflation port, wherein:
      the substance supply mechanism is configured to aspirate a fluid from a body vessel when operably coupled to the aspiration mechanism connector that is operably coupled to an aspiration port lumen, wherein the aspiration port lumen is at least partially disposed within the manifold casing;
      the substance supply mechanism is configured to infuse a fluid into a body vessel when operably coupled to the infusion mechanism connector that is operably coupled to an infusion port lumen, wherein the infusion port lumen is at least partially disposed within the manifold casing; and
      the substance supply mechanism, when operably coupled to the balloon inflation port, is configured to independently inflate a proximal balloon and a distal balloon based upon a position of a balloon selection valve, the balloon selection valve having (1) a first position, wherein the first position allows fluid communication between a balloon inflation mechanism lumen and a proximal balloon lumen operably coupled to the proximal balloon, (2) a second position, wherein the second position allows fluid communication between the balloon inflation mechanism lumen and a distal balloon lumen operably coupled to the distal balloon, and (3) a third position, wherein the third position precludes fluid communication between the balloon inflation mechanism lumen and either of the proximal balloon lumen or the distal balloon lumen, and
   providing a substance, via the substance supply mechanism, to the aspiration mechanism connector, infusion mechanism connector, or balloon inflation port.

2. The method of claim 1, wherein the substance supply mechanism comprises a balloon inflation mechanism, the balloon inflation mechanism being configured to independently adjust an inflation level of a distal balloon and a proximal balloon of the multi-lumen device via the distal balloon lumen and the proximal balloon lumen respectively.

3. The method of claim 1, further comprising a balloon selection mechanism having a balloon selection knob.

4. The method of claim 1, wherein the balloon selection valve is a three-way open/close valve.

5. The method of claim 2, wherein the balloon inflation mechanism comprises an inflation fluid-filled syringe operably coupled to the balloon inflation port.

6. The method of claim 2, wherein:
   the balloon inflation mechanism comprises a balloon inflation knob operably coupled to an inflation chamber;
   the inflation chamber houses an inflation fluid;
   the inflation chamber is disposed inside the manifold; and
   the inflation chamber comprises a plunger that, in operation, is either depressed or retracted in response to adjustment of the balloon inflation knob.

7. The method of claim 2, further comprising providing, via an agent dispersal mechanism and an infusion mechanism operably coupled to the infusion mechanism connector, a chemical agent to the infusion port lumen.

8. The method of claim 3, wherein the balloon selection knob comprises:

a closed first position that precludes fluid communication from the balloon inflation mechanism to both the distal balloon and the proximal balloon;

a second position that precludes fluid communication from the balloon inflation mechanism to the distal balloon and allows fluid communication from the balloon inflation mechanism to the proximal balloon; and a third position that precludes fluid communication from the balloon inflation mechanism to the proximal balloon and allows fluid communication from the balloon inflation mechanism to the distal balloon.

9. The method of claim 7, wherein the infusion mechanism is disposed inside the manifold casing.

10. A manifold for controlling a multi-lumen device system, the manifold comprising:

a manifold casing comprising:

an aspiration mechanism connector;

an infusion mechanism connector; and a balloon inflation port, wherein each of the aspiration mechanism connector, the infusion mechanism connector, and the balloon inflation port is configured to independently engage a substance supply mechanism;

an aspiration port lumen at least partially disposed within the manifold casing and operably coupled to the aspiration mechanism connector;

an infusion port lumen at least partially disposed within the manifold casing and operably coupled to the infusion mechanism connector;

a proximal balloon lumen at least partially disposed within the manifold casing;

a distal balloon lumen at least partially disposed within the manifold casing;

a balloon inflation mechanism lumen disposed within the manifold casing and operably coupled to the balloon inflation port and each of the proximal balloon lumen and the distal balloon lumen;

a balloon selection valve disposed within the manifold casing and operably coupled to the balloon inflation mechanism lumen and each of the proximal balloon lumen and the distal balloon lumen; and a balloon selection mechanism operably coupled to the balloon selection valve and configured to, via the balloon selection valve, selectively (1) allow fluid communication between the balloon inflation mechanism lumen and the proximal balloon lumen, (2) allow fluid communication between the balloon inflation mechanism lumen and the distal balloon lumen, or (3) preclude fluid communication between the balloon inflation mechanism lumen and either of the proximal balloon lumen or the distal balloon lumen, wherein the manifold is configured to allow independent inflation and deflation of a proximal balloon and a distal balloon disposed within a body vessel, and wherein the manifold is further configured to selectively allow aspiration and infusion of a portion of the body vessel via the aspiration mechanism connector and the infusion mechanism connector, respectively.

11. The manifold of claim 10, wherein the balloon selection mechanism further comprises a balloon selection knob.

12. The manifold of claim 10, further comprising a balloon inflation mechanism, wherein the balloon inflation mechanism comprises an inflation fluid-filled syringe operably coupled to the balloon inflation port.

13. The manifold of claim 10, wherein:

the balloon inflation mechanism comprises a balloon inflation knob operably coupled to an inflation chamber;

the inflation chamber houses an inflation fluid;

the inflation chamber is disposed inside the manifold; and the inflation chamber comprises a plunger that, in operation, is either depressed or retracted in response to adjustment of the balloon inflation knob.

14. The manifold of claim 10, further comprising an agent dispersal mechanism and an infusion mechanism operably coupled to the infusion mechanism connector, the agent dispersal mechanism being configured to cause the infusion mechanism to provide a chemical agent to the infusion port lumen.

15. The manifold of claim 10, wherein the balloon selection valve is a three-way open/close valve.

16. The manifold of claim 11, wherein the balloon selection knob comprises:

a closed first position that precludes fluid communication from the balloon inflation mechanism to both the distal balloon lumen and the proximal balloon lumen;

a second position that precludes fluid communication from the balloon inflation mechanism to the distal balloon lumen and allows fluid communication from the balloon inflation mechanism to the proximal balloon lumen; and a third position that precludes fluid communication from the balloon inflation mechanism to the proximal balloon lumen and allows fluid communication from the balloon inflation mechanism to the distal balloon lumen.

17. The manifold of claim 14, wherein the infusion mechanism is disposed inside the manifold casing.

* * * * *